(12) United States Patent
Dariani et al.

(10) Patent No.: US 12,251,405 B2
(45) Date of Patent: Mar. 18, 2025

(54) SPRAY DRIED FOLLISTATIN PRODUCT

(71) Applicant: MYOS RENS TECHNOLOGY INC., Cedar Knolls, NJ (US)

(72) Inventors: Maghsoud Dariani, Cedar Knolls, NJ (US); Neerav Padliya, Cedar Knolls, NJ (US); Alexander Tess, Cedar Knolls, NJ (US)

(73) Assignee: MYOS CORP., Cedar Knolls, NJ (US)

( * ) Notice: Subject to any disclaimer, the term of this patent is extended or adjusted under 35 U.S.C. 154(b) by 699 days.

(21) Appl. No.: 16/151,601

(22) Filed: Oct. 4, 2018

(65) Prior Publication Data

US 2020/0108102 A1 Apr. 9, 2020

Related U.S. Application Data

(60) Provisional application No. 62/740,517, filed on Oct. 3, 2018.

(51) Int. Cl.
*A61K 35/57* (2015.01)
*A23B 5/03* (2006.01)
*A23L 15/00* (2016.01)
*A23L 33/18* (2016.01)

(52) U.S. Cl.
CPC ............... *A61K 35/57* (2013.01); *A23B 5/03* (2013.01); *A23L 15/00* (2016.08); *A23L 33/18* (2016.08)

(58) Field of Classification Search
None
See application file for complete search history.

(56) References Cited

U.S. PATENT DOCUMENTS

| 2,065,114 | A | * | 12/1936 | Cahn | G01N 21/41 |
| | | | | | 436/164 |
| 4,072,570 | A | * | 2/1978 | Williams | B01D 1/18 |
| | | | | | 159/48.1 |
| 8,815,320 | B2 | | 8/2014 | Buxmann et al. | 426/244 |
| 2007/0275036 | A1 | | 11/2007 | Green et al. | 424/439 |
| 2015/0257405 | A1 | * | 9/2015 | Kelly | A23F 5/02 |
| | | | | | 426/45 |
| 2018/0368425 | A1 | * | 12/2018 | Buxmann | A23L 3/015 |

FOREIGN PATENT DOCUMENTS

| CN | 97105070 A | * | 8/1998 | |
| CN | 201210582232 A | * | 3/2013 | |
| EP | 13197015 A | * | 6/2015 | A23L 3/32 |

OTHER PUBLICATIONS

PCT/US2019/054184, publication date: Sep. 4, 2020 (Year: 2020).*
JJ: johnjuanb 1: Absorption Profile and Hormonal Influence of Fertilized Egg Yolk Ingestion in the Human; published Aug. 3, 2015 at: https://www.professionalmuscle.com/forums/index.php?threads/follistatin-in-fertile-avian-eggs. 126239/ (Year: 2015).*

* cited by examiner

*Primary Examiner* — Patricia A George

(57) ABSTRACT

Processes for production of a composition containing active follistatin via spray/heat drying of a biological source containing follistatin as well as compositions containing this active follistatin and methods it use increasing muscle mass are provided.

6 Claims, No Drawings

SPRAY DRIED FOLLISTATIN PRODUCT

This application claims the benefit of priority from U.S. Provisional Application No. 62/740,517, filed Oct. 3, 2018, teachings of which are herein incorporated by reference in their entirety.

INTRODUCTION

Field

Described herein are products containing follistatin, methods for preparing such products, methods for formulating such products and methods of using such products for increasing muscle mass.

Background

Wasting of skeletal muscle is a serious health condition that accompanies many conditions, diseases or disorders. Wasting of skeletal muscle also accompanies ageing. One of the most devastating but least-discussed aspects of age-related decline is the onset of frailty, i.e., the progressive loss of robustness in multiple tissues and organ systems. On the other side of the scale, many athletes benefit from an increase in muscle mass.

Published U.S. Patent Application No. 2007/0275036 discloses an avian follistatin product and methods for producing such products which are effective for a variety of conditions including increasing muscle mass. At page 14, paragraphs [0176]-[0179] of this published patent application, a study is disclosed indicating that fertile egg yolk cannot be spray/heat dried in order to preserve active follistatin.

U.S. Pat. No. 8,815,320 discloses a process for producing a composition containing biologically active follistatin from a biological source. Exemplified process steps involve various preservation steps while maintaining the temperature at or below 38° C. followed by freeze drying preferably at or below 42° C.

There is a need for alternative methods for production of active follistatin.

SUMMARY

An aspect of the present invention relates to a process for production of a composition comprising active follistatin via spray/heat drying of a biological source containing follistatin.

Another aspect of the present invention relates to compositions containing active follistatin obtained by spray/heat drying of a biological source containing follistatin.

Yet another aspect of the present invention relates to methods for increasing muscle mass in a subject in need thereof by administering to the subject a composition containing active follistatin obtained by spray/heat drying of a biological source containing follistatin.

DETAILED DESCRIPTION

Follistatin has been found to be a secreted glycoprotein having activity to inhibit members of the TGF-$\beta$ family, preferably to inhibit myostatin. Upon ingestion, the composition has activity to support, induce and/or positively regulate the increase of muscle in humans and animals. The composition is therefore suitable for use as a food ingredient or nutrition additive for humans and animals, e.g. for use as a compound for improving muscle increase and/or muscle regeneration.

Contrary to teachings of published U.S. Patent Application No. 2007/0275036, the inventors herein have now found that compositions comprising active follistatin can be produced via spray/heat drying of a biological source containing follistatin.

In one nonlimiting embodiment, the process for producing the composition, and the composition itself, are free from added chemical preservatives. In one nonlimiting embodiment, the process for producing the composition, and the composition, respectively, essentially consist of the natural components of the biological source or starting material. In one nonlimiting embodiment, the biological source is egg and its components, preferably egg yolk optionally including the white of egg, only subject to the physical treatment steps of the process. In the alternative to egg yolk, white of egg, which is also called egg white or egg albumen, and whole egg can be subjected to the steps of the process. In one nonlimiting embodiment, the egg is avian egg. In one nonlimiting embodiment, the avian egg is a fertilized avian egg. In one non limiting embodiment, the fertilized avian egg is from a domestic fowl selected from a turkey, chicken, duck, goose and ostrich. In another non-limiting embodiment, the biological source is raw animal blood serum.

In one nonlimiting embodiment, fertilized avian eggs are obtained from hens. The eggs are collected and stored in a refrigerator or cold room (at or lower than 4° C. (40° F.)) until they are ready to be processed. The fertilized eggs are used within 3 weeks.

The following methods for the preparation of avian follistatin powder may be carried out using whole eggs, whole egg yolks or egg yolk membranes. Whole eggs, whole egg yolks, or egg yolk membranes are homogenized or agitated strongly to form an emulsion. The agitation may be carried out by means of a mechanical stirrer. If desired, water may be added to the homogenizer. In one nonlimiting embodiment, the whole eggs, egg yolks or egg yolk membranes are diluted with deionized water to a solids concentration of ranging from about 15% to about 40%. In one nonlimiting embodiment, the whole eggs, egg yolks or egg yolk membranes are diluted with deionized water to a solids concentration of approximately 25%. The emulsified egg, egg yolks or egg yolk membranes are then transferred to a spray/heat drying apparatus and spray/heat dried to form a powder comprising active follistatin. In one nonlimiting embodiment, spray drying is performed at an inlet temperature of about 280° F. to about 390° F. and an outlet temperature of about 160° F. to about 190° F.

In some nonlimiting embodiments, the biological source for follistatin and/or the resulting powder following spray/heat drying is subjected to a preservation step to reduce any bacterial contamination. Nonlimiting examples of preservation steps include irradiation, thermal pasteurization, high pressure treatment and/or pulsed electric field treatment.

In one nonlimiting embodiment, the biological source for follistatin and/or the resulting powder following spray/heat drying is irradiated with Ebeam or gamma irradiation at levels of at least 27.5 kilo grades.

In one nonlimiting embodiment, the preservation step comprises subjecting the biological source for follistatin and/or the resulting powder following spray/heat drying to a pressure of at least 4000 bar, for at least 1 minute, preferably to 5500-6500 bar, more preferably to 6000 bar for at least 1 minute, preferably for 3 minutes, more preferably for at least 5 minutes, preferably using an adiabatic compression and pressure release, and/or pulsed electric field treatment at an electric field strength of 5 to 40 kV/cm, preferably using unipolar pulses having a pulse duration of 5 to 20 µs, preferably of 10 µs, at a repetition rate of 70 to 200 Hz, especially positive, rectangular pulses.

In one nonlimiting embodiment, the preservation step comprises thermal pasteurization wherein the egg yolk powder is stored in a hot room at about 55 to about 80° C. for about 5 to 15 days.

In some nonlimiting embodiments, the resulting product is pathogen tested to CDER and CBER standards.

In some nonlimiting embodiments, quality assurance is conducted to determine the follistatin content of the spray/heat dried powder. In some nonlimiting embodiments, the levels of active follistatin in the spray/heat dried powder approximated or determined in the composition using a method selected from Bradford protein assay, gel electrophoresis, mass spectrometry, microscopy, protein immunostaining, immunoprecipitation, a Western blot, spectrophotometry, an enzyme assay, ELISA, follistatin standardization, or combinations thereof.

The spray/heat dried active follistatin containing powder is then processed by methods known in the art or as described herein and stored. The final formulation is in compliance with standards set forth by government agencies, such as the Food and Drug Administration (FDA).

Follistatin containing products may be administered to those individuals desiring or needing muscle regeneration or increases in muscle mass. In some situations, follistatin containing products may be consumed by athletes desiring an increase in muscle mass. In other situations, follistatin products may be given to the elderly, in whom muscle mass has been lost due to ageing. In other situations, muscle mass may have been lost due to health conditions, diseases or disorders and thus follistatin containing products may be beneficial to these individuals. In some other situations, follistatin containing products may be beneficial for those individuals that satisfy a number of the aforementioned conditions or situations.

Nonlimiting examples for products comprising active follistatin prepared by spray/heat drying include sports nutrition products, dietary supplement products, nutraceutical products, health nutrition products, over-the-counter drug products, prescription drug products, and veterinary (pet or livestock) drug products.

The compositions described herein can be formulated for administration to a subject via any conventional means including, but not limited to, oral, or buccal. As used herein, the term "subject" is used to mean an animal, preferably a mammal, including a human or non-human. The terms patient and subject may be used interchangeably.

Moreover, the follistatin containing compositions described herein, can be formulated into any suitable dosage form, including but not limited to, aqueous oral dispersions, liquids, gels, syrups, elixirs, slurries, suspensions and the like, for oral ingestion by an individual in need, solid oral dosage forms, controlled release formulations, fast melt formulations, effervescent formulations, lyophilized formulations, tablets, powders, pills, dragees, capsules, delayed release formulations, aqueous liquid dispersions, self-emulsifying dispersions, solid solutions, liposomal dispersions, solid dosage forms, powders, tablets, capsules, pills, delayed release formulations.

Formulations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including glucose, fructose, lactose, sucrose, mannitol, sorbitol, *stevia* extract, or sucralose; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Formulations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, pellets, granules. In other embodiments, the pharmaceutical formulation is in the form of a powder. In still other embodiments, the pharmaceutical formulation is in the form of a tablet. Additionally, formulations described herein may be administered as a single capsule or in multiple capsule dosage form. In some embodiments, the formulation is administered in two, or three, or four, capsules or tablets.

Soft gel or soft gelatin capsules may be prepared, for example, without limitation, by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

In some embodiments, the formulations may include other medicinal or pharmaceutical agents, carriers, diluents, dispersing agents, suspending agents, thickening agents, adjuvants, such as preserving, stabilizing, wetting or emulsifying agents, solution promoters, and/or buffers. In addition, the formulations can also contain other therapeutically valuable substances.

The formulations described herein can include follistatin product and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Formulations including the spray/heat dried follistatin powder described herein may be manufactured in a conventional manner, such as, by way of example only, by means of conventional mixing, dissolving, granulating, dragee-making, levigating, emulsifying, encapsulating, entrapping or compression processes.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Binders imparting cohesive qualities may also be used. Examples include, but are not limited to, alginic acid and salts thereof; cellulose derivatives such as carboxymethylcellulose, methylcellulose, hydroxypropylmethylcellulose, hydroxyethylcellulose, hydroxypropylcellulose, ethylcellulose, and microcrystalline cellulose; microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose, glucose, dextrose, molasses, mannitol, sorbitol, xylitol, and lactose; a natural or synthetic gum such as acacia, tragacanth, ghatti gum, mucilage of isapol husks, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder.

Formulators skilled in art can determine the binder level for the formulations, but binder usage level of up to 70% in tablet formulations is common.

Compositions may further comprise carriers of relatively nontoxic chemical compounds or agents that facilitate the incorporation of a compound into cells or tissues. Nonlimiting examples include binders, suspending agents, disintegration agents, filling agents, surfactants, solubilizers, stabilizers, lubricants, wetting agents, diluents, and the like. Suitable carriers for use in solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Dispersing agents and/or viscosity modulating agents include materials that control the diffusion and homogeneity of a compound through liquid media or a granulation method or blend method. In some embodiments, these agents also facilitate the effectiveness of a coating or eroding matrix. Nonlimiting examples of diffusion facilitators/dispersing agents include hydrophilic polymers, electrolytes, a Tween, PEG, polyvinylpyrrolidone, and carbohydrate-based dispersing agents such as hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers, block copolymers of ethylene oxide and propylene oxide; and poloxamines, tetrafunctional block copolymers derived from sequential addition of propylene oxide and ethylene oxide to ethylenediamine, polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

Compositions of the present invention may further comprise diluents used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose; dibasic calcium phosphate, dicalcium phosphate dihydrate; tricalcium phosphate, calcium phosphate; anhydrous lactose, spray-dried lactose; pregelatinized starch, compressible sugar; mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; sodium chloride; inositol, bentonite, and the like.

Compositions may further comprise an enteric coating, a substance that remains substantially intact in the stomach but dissolves and releases the follistatin in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

In addition, the compositions may comprise an erosion facilitator, a material that controls the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

Filling agents including compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like can also be included in the compositions. Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

In addition, flavoring agents and/or sweeteners can be used in the compositions and may include acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

The compositions may further comprise lubricants and/or glidants that prevent, reduce or inhibit adhesion or friction of materials. Nonlimiting examples of lubricants include stearic acid, calcium hydroxide, talc, sodium stearyl fumerate, a hydrocarbon such as mineral oil, or hydrogenated vegetable oil such as hydrogenated soybean oil, higher fatty acids and their alkali-metal and alkaline earth metal salts, such as aluminum, calcium, magnesium, zinc, stearic acid, sodium stearates, glycerol, talc, waxes, boric acid, sodium benzoate, sodium acetate, sodium chloride, leucine, a polyethylene glycol (e.g., PEG-4000) or a methoxypolyethylene glycol, sodium oleate, sodium benzoate, glyceryl behenate, polyethylene glycol, magnesium or sodium lauryl sulfate, colloidal silica, a starch such as corn starch, silicone oil, a surfactant, and the like.

Plasticizers, compounds used to soften the microencapsulation material or film coatings to make them less brittle may also be included in the compositions. Examples of suitable plasticizers include, but are not limited to, polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

The compositions may further comprise solubilizers such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

In addition, the compositions my comprise stabilizers such as antioxidation agents, buffers, acids, preservatives and the like.

Suitable suspending agents for use in solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants including compounds such as sodium lauryl sulfate, sodium docusate, Tweens, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide and the like may also be included. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

Viscosity enhancing agents including, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof may also be included.

In addition, wetting agents including compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like may be included in these compositions.

In some embodiments, solid dosage forms, e.g., tablets, capsules, are prepared by mixing the spray/heat dried follistatin powder described herein, with one or more pharmaceutical excipients to form a bulk blend composition. When referring to these bulk blend compositions as homogeneous, it is meant that the particles of follistatin powder described herein, are dispersed evenly throughout the composition so that the composition may be readily subdivided into equally effective unit dosage forms, such as tablets, pills, and capsules.

Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., "The Theory and Practice of Industrial Pharmacy" (1986).

It should be appreciated that there is considerable overlap between additives used in the solid dosage forms described herein. Thus, the above-listed additives should be taken as merely exemplary, and not limiting, of the types of additives that can be included.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials which sufficiently isolate the compound from other non-compatible excipients. Materials compatible the follistatin powder described herein are those that delay the release of the follistatin product in vivo.

In other embodiments, the formulations described herein, which include the spray/heat dried follistatin powder described herein, are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734.

Instill other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components. The enteric coated oral dosage form may also be a capsule (coated or uncoated) containing pellets, beads or granules of the solid carrier or the composition.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating for the methods and compositions described herein to achieve delivery to the lower gastrointestinal tract.

In some embodiments, formulations are provided that include particles of the follistatin powder described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the spray/heat dried follistatin powder described herein, the liquid dosage forms may include additives, such as: (a) disintegrating agents; (b) dispersing agents; (c) wetting agents; (d) at least one preservative, (e) viscosity enhancing agents, (t) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. Instill another embodiment, no agitation is necessary to maintain a homogeneous aqueous dispersion.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

In one nonlimiting embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butylenegycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the formulations described herein can be self-emulsifying drug delivery systems (SEDDS). Emulsions are dispersions of one immiscible phase in another, usually in the form of droplets. Generally, emulsions are created by vigorous mechanical dispersion.

SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563.

Buccal formulations that include spray/heat dried follistatin powder described herein may be administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the follistatin product described herein, and any other components that may be present in the buccal dosage unit. Generally, the polymeric carrier comprises hydrophilic (water-soluble and water-swellable) polymers that adhere to the wet surface of the buccal mucosa. Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

In certain embodiments, delivery systems for pharmaceutical compounds may be employed, such as, for example, liposomes and emulsions. In certain embodiments, compositions provided herein can also include a mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

The compositions containing the follistatin products described herein can be administered for prophylactic and/or therapeutic treatments. In one nonlimiting embodiment, the compositions are administered to a subject already suffering from a disease or condition, in an amount sufficient to improve muscle mass. Amounts effective for this use will depend on the severity and course of the disease or condition, previous therapy, the subject's health status, weight, and the judgment of the treating health care provider. In prophylactic applications, compositions containing follistatin products described herein are administered to a subject requiring or desiring increase in muscle mass. In this use, the precise amounts also depend on the subject's state of health, weight, and the like. It is considered well within the skill of the art for one to determine such prophylactically effective amounts by routine experimentation (e.g., a dose escalation clinical trial). When used in a subject, effective amounts for this use will depend on the severity and course of the disease, disorder or condition, previous therapy, the subject's health status and response to the drugs, and the judgment of the health care provider.

The present invention also provides kits and articles of manufacture with the follistatin containing compositions. Such kits can further include a carrier, package, or container that is compartmentalized to receive one or more containers such as vials, tubes, and the like, each of the container(s) including one of the separate elements to be used in a method described herein. Suitable containers include, for example, bottles, vials, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment. A wide array of formulations of the compounds and compositions provided herein are contemplated as are a variety of treatments for any disease, disorder, or condition that would benefit by administration of follistatin and increases in muscle regeneration.

Such kits or article of manufacture optionally include a formulation as described herein with an identifying description or label or instructions relating to its use in the methods described herein.

A kit typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, carrier, package, container, labels listing contents and/or instructions for use, and package inserts with instructions for use. A set of instructions will also typically be included.

A label can be on or associated with the container. A label can be used to indicate that the contents are to be used for a specific therapeutic application. The label can also indicate directions for use of the contents, such as in the methods described herein.

The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing the follistatin products described herein formulated in a compatible carrier can also be prepared, placed in an appropriate container, and labeled for treatment of an indicated condition.

The following nonlimiting example is provided to further illustrate the present invention.

EXAMPLE

Fertilized, egg yolk was diluted with deionized water to a solids concentration of approximately 25% and then spray-dried under the following conditions:
Inlet Temperature: 380° F./193° C.
Outlet Temperature: 170° F./77° C.
The resulting egg yolk powder was analyzed for active follistatin using an ELISA assay (R&D Systems) according to the manufacturer's instructions. In parallel, active follistatin analysis was also performed on a fertilized, freeze-dried egg yolk sample. Follistatin Concentration in the fertilized, spray-dried egg yolk powder was 7.2 ng/g while follistatin concentration in the fertilized, freeze-dried egg yolk powder was 9.0 ng/g.

What is claimed is:

1. A process for production of a powder comprising active avian follistatin for oral ingestion by a subject, said method comprising:
   providing avian whole eggs, avian whole egg yolks, avian egg white or avian egg yolk membranes containing active avian follistatin;
   homogenizing or agitating the avian whole eggs, avian whole egg yolks, avian egg white, or avian egg yolk membranes to form an emulsion;
   spray drying the emulsion with heat at an inlet temperature of about 280° F. to about 390° F. and an outlet temperature of about 160° F. to about 190° F.;
   wherein said method produces a powder containing the active avian follistatin determined by enzyme-linked immunosorbent assay (ELISA); and
   formulating said powder for oral ingestion by a subject.

2. The process of claim 1 wherein the avian whole eggs, avian whole egg yolks, avian egg whites or avian egg yolk membranes are from fertilized avian eggs.

3. The process of claim 1 further comprising:
   preserving the avian whole eggs, avian whole egg yolks, avian egg whites or avian egg yolk membranes and/or powder comprising the active avian follistatin to reduce any bacterial contamination.

4. The process of claim 3 wherein the preservation step comprises irradiation, thermal pasteurization, high pressure treatment and/or pulsed electric field treatment.

5. The process of claim 1 wherein the avian whole eggs, avian whole egg yolks, or avian egg yolk membranes are diluted to a solids concentration ranging from about 15% to about 40% prior to homogenizing.

6. The process of claim 1 wherein avian eggs are collected and stored in a refrigerator or cold room at or lower than 40° F. until they are ready to be processed.

* * * * *